(12) United States Patent
Abrams et al.

(10) Patent No.: US 6,284,752 B1
(45) Date of Patent: *Sep. 4, 2001

(54) PHARMACEUTICAL COMPOSITIONS COMPRISING METAL COMPLEXES

(75) Inventors: Michael J Abrams, Glenmore, PA (US); Simon P Fricker; Barry A Murrer, both of Berkshire (GB); Owen J Vaughan, Stockholm (SE)

(73) Assignee: AnorMED Inc., Langley (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/175,028

(22) Filed: Oct. 19, 1998

Related U.S. Application Data

(63) Continuation of application No. 08/602,814, filed as application No. PCT/GB94/01817 on Aug. 19, 1994, now Pat. No. 5,824,673.

(30) Foreign Application Priority Data

Aug. 25, 1993 (DE) ................................................ 93 17 686

(51) Int. Cl.$^7$ ........................ A61K 31/555; A61K 31/295
(52) U.S. Cl. ............................ 514/184; 514/158; 514/501
(58) Field of Search ..................................... 514/184, 185, 514/501

(56) References Cited

FOREIGN PATENT DOCUMENTS

WO 91/13553    9/1991   (WO) .

OTHER PUBLICATIONS

Alessio, E.A. et al. "cis–and trans–Dihalotetrakis(dimethyl sulfoxide)ruthenium(II) Complexes," *Inorganic Chemistry* (1988)27:4099–4106.

Alessio, E. et al. "Synthesis, Molecular Structure, and Chemical Behavior of Hydrogen *tans*–Bis(dimethyl sulfoxide)tetrachlororuthenate(III) and mer–Trichlorotris(dimethyl sulfoxide)ruthenium(III): The First Fully Charaterized Chloride–Dimethyl Sulfoxide–Ruthenium(III) Complexes," *Inorganic Chemistry* (1991) 30:609–618.

Allen, A.D. et al. "Ruthenium Complexes Containing Molecular Nitrogen," *Journal American Chemical Society* (Oct. 25, 1967) 89(22):5595–5599.

Bajaj, H. C. *et al.* "Kinetics and Mechanism of the Ligand Substitution Reactions of N–(hydroxyethyl)ethylenediaminetriacetate Complexes of Ruthenium(III) in Aqueous Solution," *Inorganic Chemistry* (1982) 28:1980–83.

Bino, A. et al. "Structural Studies of Some Multiply bonded Diruthenium Tetracarboxylate Compounds," *Inorganic Chemistry* (1979) 18(9):2599–2604.

Bryant, G. M. et al. "Charge–Transfer and Intraligand Electronic Spectra of Bipyridyl Complexes of Iron, Ruthenium, and Osmium," *Aust J Chem* (1971) 24(2):257–73.

Buckingham, D.A. et al. "Mono–and Bis–(2,2'–Bipyridine) and (1,10–Phenanthroline) Chelates of Ruthenium and Osmiun," *Aust J Chem* (1964) 17:325–336.

Chan, P.K. et al. "Convenient Synthesis of trans–Dichlororotetraamineruthenium(III) Cations," *Inorganic Chemistry* (1975) 14(10):2579–2580.

Che, C–M. et al. "Cis Ruthenium Complexes of 1,4,8,11–Tetraazacyclotetradecane (cyclam): Crystal and molecular Structure of cis –[Ru(cyclam)Cl$_2$]Cl," *Inorganic Chemistry* (1985) 24:1359–1363.

Diamantis, A.A. et al. "Preparation and Structure of Ethylenediaminetetraacetate Complexes of ruthenium(II) with Dinitrogen, Carbon Monoxide, and Other π–Acceptor Ligands," *Inorganic Chemistry* (1981) 20:1142–1150.

Diamantis, A. A. et al. "Preparation and Coordination Geometry of Quadridentate Ethylenediaminetetraacetate Complexes of Ruthenium(II) and –(III)," *Inorganic Chemistry* (1983) 22:1934–1936.

Gilbert, J. D. et al. "Preparative Use of Blue Solutions of ruthenium(II): Ruthenium–(II) and –(III) Complexes with Amines, Nitriles, Phosphines, etc.," *Journal Chemical Society* (A) (1970):2765–2769.

Greaves, S. J. et al. "Surface–Enhanced Spectroscopy (SERS) of Ligands and Their Complexes on Silver Sols —I. Maltol, Tropolone and their Complexes with Group VIII and Group VI Metals," *Polyhedron* (1988) 7(19/20):1973–1979.

Hendrickson, A. R. et al. "Tris–and Pentakis–dialkyldithiocarbamates of Ruthenium, [Ru(S$_2$CNR$_2$)$_3$]$^n$ and [Ru$_2$(S$_2$CNR$_2$)$_5$]$^n$ (n=+1,0, and -): Chemical and Electrochemical Interrelations," *Journal Chemical Society Dalton Transactions* (1976) 20:2032–2039.

Henn, M. et al. "Ruthenium(II)–dimethyl sulfoxide complexes with nitrogen ligands: Synthesis, characterization and solution chemistry. The crystal structures of cis, fac–RuCl$_2$(DMSO)$_3$(NH$_3$) and trans,cis, cis–RuCl$_2$(DMSO)$_2$(NH$_3$)$_2$·H$_2$O," *Inorganica Chimica Acta* (1991) 187:39–50.

(List continued on next page.)

Primary Examiner—Kevin E. Weddington
(74) Attorney, Agent, or Firm—Morrison & Foerster LLP

(57) ABSTRACT

New pharmaceutical compositions and pharmaceutical compositions comprising metal complexes have activity against diseases caused by or related to overproduction or localised high concentration of nitric oxide in the body.

4 Claims, 2 Drawing Sheets

OTHER PUBLICATIONS

Figure 1:
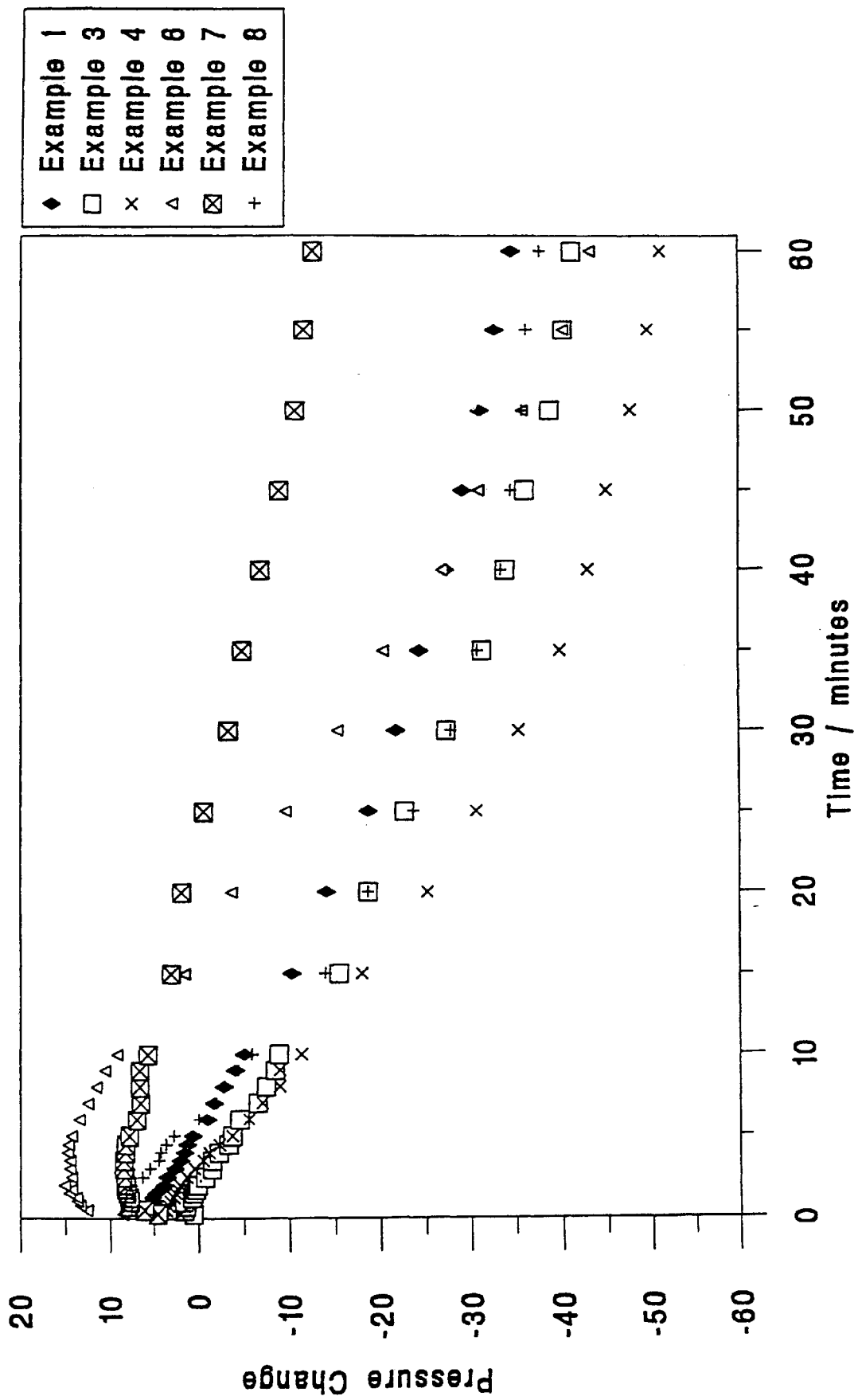

James, B. R. et al. "A Convenient Synthesis of Potassium Hexachlororuthenate(III), and Potassium Tetrachloromono-(Bipyridine)Ruthenate(III) and Analogous Mono (Phenanthroline) Complex," *Inorg Nucl Chem Letters* (1975) 11(12):837–839.

Kasahara, Y. et al. "Reaction of Tris(β–diketonatoruthenium(III) Complexes with Strong Acids in Acetonitrile, Formation of Bis(acetonitrile)bis(β–diketonato)ruthenium(III) Complexex," *Chemistry Latters* (1990) 3:381–384.

Ke, M. et al. "Five–Co–ordinate Arly–and Alkyl–Ruthenium(III) Porphyrin Complexes, and Ruthenium–Carbon Bond Strengths," *Journal Chemical Society, Chem Commun* (1987) 1110–1112.

Konings, M. S. et al. "Gadolinium Complexation by a New DTPA–Amide Ligand. Amide Oxygen Coordination," *Inorganic Chemistry* (1990) 29:1488–1491.

Meyer, T. J. et al. "Electron–Transfer Reactions of ruthenium Ammines," *Inorganic Chemistry* (Nov. 1968) 7(11):2369–2379.

Mitchell, R. W. et al. "Carboxylato–triphenylphosphine Complexes of ruthenium, Cationic Triphenylphosphine Complexes derived from them, and their Behavior as Homogeneous hydrogenation Catalysts for Alkenes," *Journal Chemical Society Dalton Transactions* (1973) 8:846–854.

Mukaida, M. et al. "Syntheses of Formato–, Acetato–, Benzoato–, and Chlorosubstituted Acetatoruthenium Complexes, and Their Properties," *Bull Chem Soc Japan* (Jul. 1972) 45(7):2143–2147.

Pell, S.D. et al. "cis–Tetraamminedihaloruthenium(III) Halide Complexes," Chapter 13, in Inorganic Syntheses, vol. 26:65–77. John Wiley & Sons, 1986.

Schwarzenbach, G. et al. "Komplexone XXIX. Ein grosser Chelateffekt besonderer Art," *Helvetica Chimica Acta* (Aug. 27, 1957) vol. 40, Fasciculus VI, No. 199:1886–1900.

Spencer, A. et al "$\mu_3$–Oxo–triruthenium Carboxylate Complexes," *Journal Chemical Society Dalton Transcations* (1972) 14:1570–1577.

Taqui Kahn, M. M. et al. "Synthesis, Characterization and Electrochemical Studies of Ruthenium(III)Aminopolycarboxylic Acid Complexes," *Journal Chemical Research (M)* (1986):1001–1009.

Taqui Kahn, M. M. et al. "Mixed–ligand Complexes of Ruthenium–(III) and–(II) with Ethylenediaminetetraacetate and Bidentate Phosphines and Arsines," *Journal Chemical Society Dalton Transactions* (Mar. 1992) 5:885–890.

Tse, P–K. et al. "Study of Structural Influence on the Formation Conststnts of Lanthanide–Polyamino Polycaraboxylate Complexes," *Inorganic Chemistry* (1985) 24:2727–2730.

Turowski, P. N. et al. "Ferric Ion Sequestering Agents. 18.[1] Two Dihydroxamic Acid Derivatives of EDTA and DTPA," *Inorganic Chemistry* (1988) 27:474–481.

Williams, N. H. et al. "Ruthenium Iron Complexes of Dipicolinic Acid: Synthesis, Solution Properties and Kinetics of Electron Transfer Reactions with Ascorbate Ions," *Aust J Chem* (1983) 36(1):2377–2386.

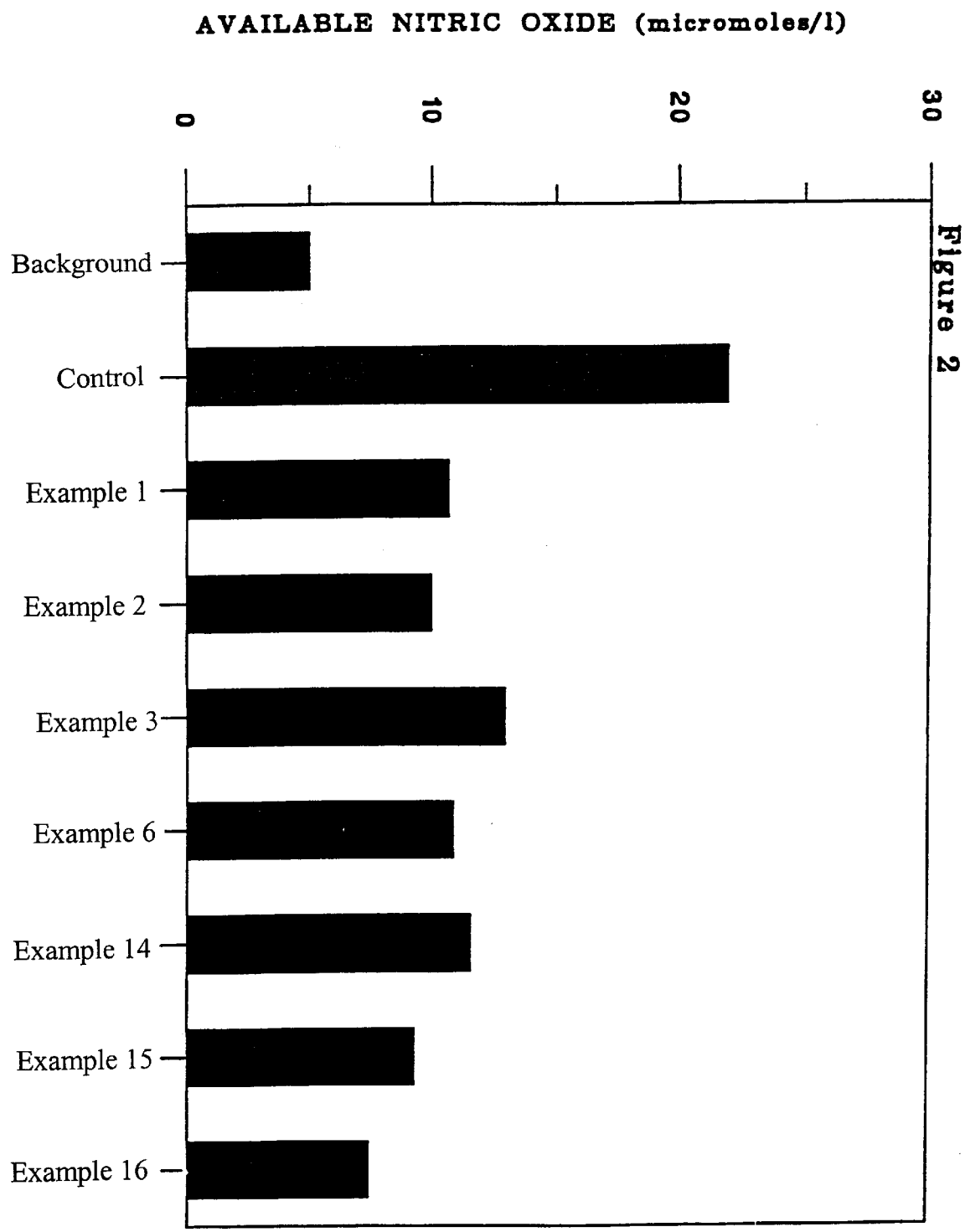

PHARMACEUTICAL COMPOSITIONS COMPRISING METAL COMPLEXES

This application is a continuation of Ser. No. 08/602,814 filed Feb. 26, 1996. U.S. Pat. No. 5,824,673, which is the U.S. national stage of application No. PCT/GB94/01817, filed Aug. 19, 1994.

This invention relates to new pharmaceutical compositions and to pharmaceutical compositions having activity against diseases caused by or related to overproduction or localised high concentration of nitric oxide in the body.

Nitric oxide (NO) plays a varied and vital role in the human body. For example, NO plays a vital role in the control of blood pressure; it acts as a neurotransmitter; it plays a role in inhibition of platelet aggregation (important in thrombosis or blockages of the blood vessels), and in cylostasis (important in fighting of tumours). Overproduction of NO however, has been implicated in a number of disease states, including vascular/pressor diseases such as septic shock, post-ischaemic cerebral damage, migraine, and dialysis induced renal hypotension; immunopathologic diseases such as hepatic damage in inflammation and sepsis, allograft rejection, graft versus host diseases, diabetes and wound healing; neurodegenerative diseases such as cerebral ischaemia, trauma, chronic epilepsy, Alzheimer's disease, Huntington's disease, and AIDS dementia complex; and side effects of treatment such as restenosis following angioplastic treatment and secondary hypotension following cytokine therapy.

Pharmacological modulation of nitric oxide in any of these disease states should prove extremely beneficial.

One above-mentioned disease relating to overproduction of NO, is septic shock. This is precipitated by local septicaemia or endotoxaemia, (high local levels of bacterial endotoxins). The result is activation of macrophages, lymphocytes, endothelial cells and other cell types capable of producing NO, further mediated by cytokine production by these cells. The activated macrophages produce excess NO which causes vasodilation of the blood vessels, and results in local vascular damage and vascular collapse. This destruction of vascular integrity may be so great that it leads to the collapse of haemodynamic homeostasis, the end result being death.

Current ideas for pharmacological modulation of nitric oxide in such diseases are based on dealing with the mediators of septic shock, such as cytokines, endotoxins, and platelet activating factor (PAF). The approaches include use of antibodies to cytokines such as tumour necrosis factor (TNF), receptor antagonists such as interleukin 1, (IL-1), antibodies to lipopolysaccharide (the endotoxin produced by gram negative bacteria, and PAF antagonists. All such approaches while challenging a factor mediating septic shock, do not attempt to deal with the aetiology, or cause, of the disease. Recent advances in understanding of NO have lead to the proposal that inhibitors of the NO synthase enzyme, such as $N^G$-monomethy-L-arginine (L-NMMA), may be useful in the treatment of septic shock and other NO overproduction related to diseases since they inhibit NO production. While these inhibitors have shown some utility in animal models and preliminary clinical studies, they have the disadvantage of undesirably inhibiting total NO synthesis in the body.

An aim of the present invention is to provide new and previously indicated pharmaceutical compositions which are able to modulate NO levels in the body by scavenging, or removing, NO in situ so that necessary NO synthesis continues while dangerous excesses are removed. We have found that certain metal complexes have the ability to carry out this important role.

Some metal complexes are known in pharmaceutical compositions for the treatment of diseases of the human body. For example, certain complexes of platinum and ruthenium have been used or indicated in the treatment of cancer. Metal complexes have not however been previously indicated in the treatment of NO overproduction related diseases.

This invention provides for the use of a neutral, anionic or cationic metal complex having at least one site for coordination with NO, of formula $$[M_a(X_bL)_cY_dZ_e]^{n\pm} \qquad \text{formula I,}$$

in the manufacture of a medicament for the attenuation of NO levels where NO is implicated in disease,
where:
  M is a metal ion or a mixture of metal ions;
  X is a cation or a mixture of cations;
  L is a ligand, or mixture of ligands each containing at least two different donor atoms selected from the elements of Group IV, Group V or Group VI of the Periodic Table;
  Y is a ligand, or a mixture of the same or different ligands each containing at least one donor atom or more than one donor atom, which donor atom is selected from the elements of Group IV, Group V or Group VI of the Periodic Table; and
  Z is a halide or pseudohalide ion or a mixture of halide ions and pseudohalide ions;
  $a=1-3$; $b=0-12$; $c=0-18$; $d=0-18$; $e=0-18$; and $n=0-10$;
  provided that at least one of c, d and e is 1 or more;
    and where c is 0; b is also 0;
    and where a is 1; c, d and e are not greater than 9;
    and where a is 2; c, d and e are not greater than 12.
  By "complex" in this specification is meant a neutral complex or anionic or cationic species.

The term "Group" which is used herein is to be understood as a vertical column of the periodic table in which elements of each Group have similar physical and chemical properties. The definition of the Periodic Table is that credited to Mendeleev; Chambers Dictionary of Science and Technology, 1974. Published by W & R Chambers Ltd.

This invention may also be stated as providing a method of attenuation of NO levels where NO is implicated in diseases of the human body, comprising administering a pharmaceutical composition containing a neutral, anionic or cationic metal complex of formula I.

This invention may also provide for the use of a neutral, anionic or cationic metal complex of formula I in the manufacture of a medicament for the treatment of NO overproduction related disease.

This invention may also be stated as providing a method of treatment of diseases of the human body resultant of overproduction of NO in the human body, comprising administering a pharmaceutical composition containing a neutral, anionic or cationic metal complex of formula I.

Where the formula I represents an anionic species, a cation will also be present. Where formula I represents a cationic species, an anion will also be present. The metal complexes may be hydrated.

Preferably, M is a first, second or third row transition metal ion. For example, M may be an Rh, Ru, Os, Mn, Co, Cr or Re ion, and is preferably an Rh, Ru or Os ion.

Suitably M is in an oxidation state III. We have found surprisingly that when the metal ion for example ruthenium is in oxidation state III, the rate at which it binds with NO is significantly faster than when it is in oxidation state II.

X may be any cation, such as a mono-, di- or tri-valent cation. Spitable cations may be H$^+$, K$^+$, Na$^+$, NH$_4^+$ or Ca$^{2+}$. Conveniently X may be H$^+$, K$^+$ or Na$^+$.

Preferably, L is a ligand containing both nitrogen and oxygen donor atoms. Examples of suitable such ligands include ethylenediamine-N,N'-diacetic acid (edda), ethylenediaminetetraacetic acid (edta), nitrilotriacetic acid (nta), dipicolinic acid (dipic), picolinic acid (pic), diethylenetriaminepentaacetic acid (dtpa), thiobis(ethylenenitrilo) tetraacetic acid (tedta), dithioethanebis(ethylenenitrilo) tetraacetic acid (dtedta) and N-(2-hydroxyethyl) ethylenediamine-triacetic acid (hedtra).

Preferably, Y is a ligand containing nitrogen, oxygen, sulphur, carbon, or phosphorus donor groups. Suitable nitrogen donor groups may be for example ammine, amine, nitrile and nitride or derivations thereof. Suitable oxygen donor groups may be for example carboxylic acid, ester or derivations thereof, water, oxide, sulphoxide, hydroxide, acetate, lactate, propionate, oxalate and maltolate. Suitable sulphur donor groups may be for example sulphoxide, dialkylsulphide, dithiocarbamate or dithiophosphate. Suitable carbon donor groups may be for example carbon monoxide or isocyanide. Suitable phosphorus donor groups may be for example trialkylphosphine.

Z may be any halide and is preferably chloride, bromide or iodide. Most conveniently, Z is chloride.

Examples of metal complexes for use according to the present invention include optionally hydrated ruthenium complexes of formula

   formula II, where L" is an amide or ester or derivative thereof, or a polydentate aminocarboxylate ligand, for example edta, nta, dipic, pic, edda, tropolone, dtpa, hedtra, tedta or dtedta or diamide of edta or dtpa or a mixture of any of these, and Y is as defined above and may for example be selected from acetylacetone (acac), a β-diketonate, water, dimethylsulphoxide (dmso), carboxylate, bidentate carboxylate, catechol, kojic acid, maltol, hydroxide, tropolone, malonic acid, oxalic acid, 2,3-dihydroxynaphthalene, squaric acid, acetate, a sulphate and a glycolate. The skilled addressee will be able to substitute other known ligands at Y and which will fall within the scope of the inventions. Preparative methods of tedta, dtedta and diamide of edta and dtpa are described in the following references respectively:

P Tse & J E Powell, Inorg Chem, (1985), 24, 2727

G Schwartzenbach, H Senner, G Anderegg, Helv Chim Acta 1957, 40, 1886

M S Konings, W C Dow, D B Love, K N Raymond, S C Quay and S M Rocklage, Inorg Chem (1990), 29, 1488–1491

P N Turowski, S J Rodgers, R C Scarrow and K N Raymond, Inorg Chem (1988), 27, 474–481.

Where the complex of formula II is an anion, a cation will be required. For example the complexes of formula II are present in K[Ru(Hedta)Cl]2H$_2$O

[Ru(H$_2$edta)(acac)]

K[Ru(hedtra)Cl]H$_2$O

K[Ru(dipic)$_2$]H$_2$O (H$_2$pic)[RuCl$_2$(pic)$_2$](Hpic)H$_2$O

K[Ru(H$_2$edta)Cl$_2$]H$_2$O

K[Ru(Hnta)$_2$]½H$_2$O

K[Ru(H$_2$dtpa)Cl]H$_2$O

[Ru(Hhedtra)acac]H$_2$O

[(Ru(Hhedtra)trop]

[Ru(H$_3$dtpa)Cl]

Complexes of formula II have not to the best of our knowledge been previously indicated in any pharmaceutical composition. Therefore the present invention also provides a pharmaceutical composition containing an optionally hydrated ruthenium complex of formula II.

Further examples of metal complexes for use according to the present invention include optionally hydrated complexes of formula III

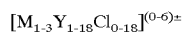   formula III

Where Y is a sulphur donor ligand. For example, such complex is present in

[Ru(mtc)$_3$] (mtc=4-morpholinecarbodithoic acid)

Ru(S$_2$CNCH$_2$CH$_2$NMeCH$_2$CH$_2$)$_3$½H$_2$O

Complexes of formula III in which Y is a sulphur donor ligand have not to the best of our knowledge been previously indicated in any pharmaceutical composition. Therefore, the present invention also provides a pharmaceutical composition containing an optionally hydrated complex of formula III wherein Y is a sulphur donor ligand.

Yet further examples of metal complexes for use according to the present invention include optionally hydrated complexes of ruthenium of formula $$[M'''_{1-3}Y'''_{1-18}Cl_{0-18}]^{(0-6)\pm}$$   formula III where M''' is ruthenium and Y''' is an oxygen-donor ligand such as acetate, lactate, water, oxide, propionate (COEt), oxalate (ox), or maltolate (maltol) or a combination of these. For example complexes of formula III are present in

[Ru$_3$O(OAc)$_6$](OAc)

[Ru$_3$O(lac)$_6$](lac)

[Ru$_2$(OAc)$_4$]NO$_3$

[Ru$_2$(OCOEt)$_4$]NO$_3$

K$_3$[Ru(ox)$_3$]

[Ru$_2$(OAc)$_4$]Cl

[Ru(maltol)$_3$]

Some complexes of formula III have not to the best of our knowledge been previously indicated in any pharmaceutical composition. Therefore the present invention also provides a pharmaceutical composition containing an optionally hydrated complex of ruthenium of formula III wherein M''' is ruthenium and Y''' is an oxygen-donor ligand selected from the group acetate, lactate, oxide, propionate and maltolate.

Further examples of metal complexes for use according to the present invention include optionally hydrated complexes of ruthenium of formula $$[RuY^{IV}_{1-9}Cl_{1-9}]^{(0-4)\pm} \quad \text{formula IV}$$

where $Y^{IV}$ is a nitrogen-donor ligand such as ammine, ethylenediamnine (en), pyridine (py), 1,10-phenanthroline (phen), 2,2-bipyridine (bipy) or 1,4,8,11-tetraazacyclotetradecane (cyclam), 2,3,7,8,12,13,17,18-octaethylporphyrin (oep) or a combination of these. For example complexes of formula IV are present in

[RU(NH$_3$)$_5$Cl]Cl$_2$

[Ru(en)$_3$]I$_3$ trans-[RuCl$_2$(py)$_4$]

K[Ru(phen)Cl$_4$]

[Ru(cyclam)Cl$_2$]Cl

K[Ru(bipy)Cl$_4$]

[Ru(NH$_3$)$_6$]Cl$_3$

[Ru(NH$_3$)$_4$Cl$_2$]Cl

Ru(oep)Ph

Some complexes of formula IV have not to the best of our knowledge been previously indicated in any pharmaceutical composition. Therefore the present invention also provides a pharmaceutical composition containing an optionally hydrated complex of ruthenium of formula IV wherein $Y^{IV}$ is a nitrogen-donor ligand selected from the group en, py, phen, bipy, cyclam and oep. Derivations of these ligands can be prepared by a skilled addressee and which will fall within the scope of the inventions.

Still further examples of metal complexes for use according to the present invention include optionally hydrated complexes of ruthenium or osmium of general formula $$[M_{1-3}Y^{V}_{1-18}Cl_{0-18}]^{(0-6)\pm} \quad \text{formula V}$$

where $Y^V$ is a combination of donor ligands such as are described hereinabove, for example ammine, dmso, oxalate, bipy, acac and MeCN. Complexes of formula V are present in for example

[Ru(NH$_3$)(dmso)$_2$Cl$_3$]

cis-[Ru(dmso)$_4$Cl$_2$]

cis-[Ru(NH$_3$)(dmso)$_3$Cl$_2$]

[Ru(dmso)$_3$Cl$_3$]

[Os(ox)(bipy)$_2$]H$_2$O

[Ru(acac)$_2$(MeCN)$_2$]CF$_3$SO$_3$

The complex ions of the latter two compounds above have not to the best of our knowledge been previously indicated in any pharmaceutical composition. Therefore the present invention also provides a pharmaceutical composition containing an optionally hydrated complex of formula [Os(ox)(bipy)$_2$]; and further a pharmaceutical composition containing an optionally hydrated complex of formula [Ru(acac)$_2$(MeCN)$_2$]$^+$.

In use the complexes of the present invention may be included as an active component in a pharmaceutical composition containing an optionally hydrated complex of any of formulae I–V, in admixture with a pharmaceutically acceptable carrier or diluent. Said pharmaceutical composition may be formulated according to well known principles, and may be in the form of a solution or suspension for parenteral administration in single or repeat doses or be in capsule, tablet, dragee, or other solid composition or as a solution or suspension for oral administration, or formulated into pessaries or suppositories, or sustained release forms of any of the above. The solution or suspension may be administered by a single or repeat bolus injection or continuous infusion, or any other desired schedule. Suitable diluents, carriers, excipients and other components are known. Said pharmaceutical composition may contain dosages determined in accordance with conventional pharmacological methods, suitable to provide active complexes in the dosage range in humans of 1 mg to 10 g per day. Actual required dosage is largely dependent on where in the body there is the excess concentration of NO and for how long overproduction continues or attenuation of NO levels, where NO is implicated in disease, is required.

This invention will now be illustrated by Example.

A number of commercially available compounds, and compounds prepared by routes known in the literature, containing the complexes of the present invention were tested in vitro, in vitro cell culture, and ex-vivo in order to determine ability to coordinate with NO. The complexes tested were as follows:

| Example | Compound | Literature Reference for Preparation |
|---|---|---|
| 1. | K[Ru(Hedta)Cl]2H$_2$O | AA Diamantis & JV Dubrawski, Inorg. Chem., (1981), 20, 1142–50 |
| 2 | [Ru(H$_2$edta)(acac)] | AA Diamantis & JV Dubrawski, Inorg. Chem., (1983), 22, 1934–36 |
| 3 | K[Ru(hedtra)Cl]H$_2$O | NH Williams & JK Yandell, Aust. J. Chem. (1983), 36(12), 2377–2386 |
| 5 | (H$_2$pic)[RuCl$_2$(pic)$_2$](Hpic)H$_2$O | JD Gilbert, D Rose & G Wilkinson, J. Chem. Soc. (A), (1970), 2765–9 |
| 6 | K[Ru(H$_2$edta)Cl$_2$]H$_2$O | AA Diamantis & JV Dubrawski, Inorg. Chem. (1981), 20, 1142–50 |
| 7 | K[Ru(Hnta)$_2$]½H$_2$O | MM Taqui Khan, A Kumar & Z Shirin, J. Chem. Research (M), (1986), 1001–1009 |
| 8 | K[Ru(H$_2$dtpa)Cl]H$_2$O | MM Taqui Khan, A Kumar & Z Shirin, J. Chem. Research (M), (1986), 1001–1009 |
| 9 | [Ru$_3$O(lac)$_6$](lac) | A Spencer & G Wilkinson, J. Chem. Soc. Dalton Trans, (1972), 1570–77 |
| 10 | [Ru$_3$O(OAc)$_6$](OAc) | A Spencer & G Wilkinson, J. Chem. Soc. Dalton Trans.. (1972), 1570–77 |
| 11 | [Ru$_2$(OAc)$_4$]NO$_3$ | M Mukaida, T Nomura & T Ishimori, Bull. Chem. Soc. Japan, (1972), 45, 2143–7 |
| 12 | [Ru$_2$(OCOEt)$_4$]NO$_3$ | A Bino, FA Cotton & TR Felthouse, Inorg. Chem. (1979), 18, |

-continued

| Example | Compound | Literature Reference for Preparation |
|---|---|---|
| 13 | $K_3[Ru(ox)_3]$ | 2599–2604 CM Che, SS Kwong, CK Poon, TF Lai & TCW Mak Inorg. Chem. (1985), 24, 1359–63 |
| 14 | $[Ru_2(OAc)_4]Cl$ | RW Mitchell, A Spencer & G Wilkinson J. Chem. Soc. Dalton Trans., (1973), 846–54 |
| 15 | $[Ru(NH_3)_5Cl]Cl_2$ | AD Allen, F Bottomley, RO Harris, VP Reinsalu & CV Senoff J. Amer. Chem. Soc. (1967), 89, 5595–5599 |
| 16 | $[Ru(en)_3]I_3$ | TJ Meyer & H Taube Inorg. Chem. (1968), 7, 2369–2379 |
| 17 | $K[RuCl_4(phen)]H_2O$ | BR James & RS McMillan Inorg. Nucl. Chem. Lett. (1975), 11(12) 837–9 |
| 18 | $[Ru(cyclam)Cl_2]Cl$ | PK Chan, DA Isabirye & CK Poon Inorg. Chem. (1975), 14, 2579–80 |
| 19 | $K[RuCl_4(bipy)]$ | BR James & RS McMillan Inorg. Nucl. Chem. Lett. (1975), 11(12), 837–9 |
| 20 | $[RuCl_3(dmso)_2(NH_3)]$ | Patent: International Publication No WO 91/13553 |
| 21 | $[Ru(NH_3)_6]Cl_3$ | Matthey Catalogue Sales: Cat No [190245] |
| 22 | cis-$[RuCl_2(dmso)_4]$ | EA Allesio, G Mestroni, G Nardin, WM Attia, M Calligaris, G Sava & S Zorget Inorg. Chem. (1988), 27, 4099–4106 |
| 23 | cis-$[RuCl_2(dmso)_3(NH_3)]$ | M Henn, E Alessio, G Mestroni, M Calligaris & WM Attia Inorg. Chim. Acta, (1991), 187, 39–50 |
| 24 | $[RuCl_3(dmso)_3]$ | E Alessio, G Balducci, M Calligaris, G Costa, WM Attia & G Mestroni Inorg. Chem. (1991), 30, 609–618 |
| 25 | $[Ru(mtc)_3]$ | AR Hendrickson, JM Hope & RL Martin J. Chem. Soc. Dalton Trans. (1976), 20, 2032–9 |
| 26 | $[Ru(maltol)_3]$ | WP Griffith & SJ Greaves Polyhedron, (1988), 7(19), 1973–9 |
| 27 | $[Ru(acac)_2(MeCN)_2]CF_3SO_3$ | Y Kasahara, T Hoshino, K Shimizu & GP Sato Chem. Lett. (1990), 3, 381–4 |
| 28 | $K_2[RuCl_5(H_2O)]$ | Matthey Catalogue Sales: Cat No [190094] |
| 29 | $[Os(ox)(bipy)_2].H_2O$ | DA Buckingham, FP Dwyer, HA Goodwin & AM Sargeson Aust. J. Chem. (1964), 325–336 GM Bryant, JE Fergusson & HKJ Powell Aust. J. Chem. (1971), 24(2), 257–73 |
| 30 | $[Ru(NH_3)_4Cl_2]Cl$ | SD Pell, MM Sherban, V Tramintano & MJ Clarke Inorg Synth, (1989), 26, 65. |
| 31 | $[Ru(hedtra)(dppm)]$ | MM Taqui Khan, K Vankatasubramanian, Z Shirin, MM Bhadbhade J Chem Soc Dalt Trans (1992), 885–890 |
| 32 | Ru(oep)Ph | M Ke, SJ Rettig, BR James and D Dolphin J Chem Soc Chem Commun (1987), 1110 |

A number of new compounds were prepared according to the following protocols. The first four compounds are examples of ruthenium complexes of formula $[Ru(H_{0-6}L'')_{1-3}Y_{0-2}Cl_{0-4}]^{(0-4)\pm}$ (formula II), the subsequent two are examples of $[M_{1-3}Y_{1-8}Cl_{0-18}]^{(0-6)\pm}$ (formula III).

Preparation of $[Ru(Hhedtra)acac].H_2O$

Excess acetylacetone (1 cm$^3$) was added to an aqueous solution (5 cm$^3$) of K[Ru(hedtra)Cl] (0.5 g). The solution colour changed to violet. The mixture was warmed for 20 minutes then left to stand at room temperature for 20 minutes. The violet solution was extracted with chloroform (20 cm$^3$). The extraction was repeated twice more. A violet product precipitated from the aqueous fraction. The product was filtered, washed in acetone and dried in vacuo, yield 0.1 g (18%). Anal. Calc. for $C_{15}H_{25}O_{10}N_2Ru$: C, 36.43; H, 5.11; N, 5.70. Found: C, 36.16; H, 5.42; N, 5.61%.

Preparation of $[Ru(Hhedtra)trop]2H_2O$

A three-fold excess of tropalone (0.78 g) dissolved in 50:50 water/absolute ethanol (5 cm$^3$) was added to a warm aqueous solution of K[Ru(hedtra)Cl] (10 cm$^3$). The mixture was heated for 1 hour. On cooling, the dark green mixture was extracted with 3×20 cm$^3$) portions of dichloromethane. On standing, a dark green product precipitated from the aqueous fraction. The product was filtered, washed with water (1 cm$^3$), ether and dried in vacuo, yield 0.4 g (36%). Anal Calc. for $C_{17}H_{22}N_2O_9Ru.2H_2O$: C, 38.13; H, 4.86; N, 5.23. Found: C, 38.55; H, 4.67; N, 5.28%.

Preparation of $[Ru(H_3dtpa)Cl]$ $K_2[RuCl_5H_2O].x315 H_2O$ (1 g) was suspended in $HClO_4$ (15 cm$^3$, 1 mM) and diethylenetriaminepentaacetic acid (1.05 g) added. The reaction mixture was heated under reflux for 1.5 hours forming a yellow/brown solution. On cooling a yellow product crystallised which was collected by filtration, washed with 90% absolute ethanol/water, diethyl ether and dried in vacuo, yield 0.75 g, 53%. Anal calcd. for $C_{14}H_{21}N_3O_{10}ClRu$: C, 31.85; H, 3.98; N, 7.96; Cl, 6.73. Found: C, 29.77; H, 3.81; N, 7.36; Cl, 6.64.

Preparation of $K[RuHHBEDCl]3H_2O$ 0.41 g of $K_2[RuCl_5]xH_2O$ was dissolved in water (20 ml). To this solution was added 1 equivalent (0.39 g) of N,N'di (2-hydroxy-benzyl)ethylenediamine N,N-diacetic acid (hbed) dissolved in water (50 ml) with KOH (0.12 g) and MeOH (1 ml). This mixture was heated at reflux for 90 minutes. Upon cooling a dark, insoluble precipitate formed. This material was removed by filtration and the resulting red-violet solution was taken to dryness by rotary evaporation. Trituration with water and washing with acetone yielded 90 mg of a dark solid. Anal. calcd. for $C_{18}H_{22}N_2O_9RuClK$: C, 36.89; H, 3.96; N, 4.78; Cl, 6.04. Found: C, 37.09; H, 4.23; N, 4.92; Cl, 6.28.

Preparation of $Ru(S_2CNCH_2CH_2NMeCH_2CH_2)_3½H_2O$ $Me_4N[S_2CNCH_2CH_2NMeCH_2CH_2]$ was made by the standard method and crystallised from methanol-ether in 71% yield.

RuCl$_3$xH$_2$O, 0.50 g, 2.15 mmol was refluxed in 30 ml of methanol for 10 minutes and cooled. 1.87 g, 7.50 mmol of Me$_4$N[S$_2$CNCH$_2$CH$_2$NMeCH$_2$CH$_2$] was added and the mixture refluxed for 16 hours. After cooling 0.72 g of crude product was filtered off, dissolved in dichloromethane and filtered. The filtrate was loaded into 15 cc of basic alumina and eluted with dichloromethane. Removal of solvent and crystallisation from dichloromethane with ether by vapour-phase diffusion gave 0.5 g, 0.80 mmol, 37% of brown-black crystals, Ru(S$_2$CNCH$_2$CH$_2$NMeCH$_2$CH$_2$)$_3$½H$_2$O. Analysis for C$_{18}$H$_{34}$N$_6$O$_5$RuS$_6$: Calc: C, 34.00; H, 5.39; N, 13.22; S, 30.25. Found: C, 34.21; H, 5.47; N, 13.12; S, 30.36.

Preparation of Ru[S$_2$P(OC$_2$H$_2$OC$_2$H$_4$OMe)$_2$]$_3$

K[S$_2$P(OC$_2$H$_4$OC$_2$H$_4$OMe)$_2$]$_3$ was made by standard method and crystallised from methanol in 76% yield.

RuCl$_3$xH$_2$O, 1.00 g, 4.30 mmol was refluxed in 50 ml of 0.1 N HCl with 1 ml of ethanol for 20 minutes and cooled. To this solution was added 5.28 g (excess) K[S$_2$P(OC$_2$H$_4$OC$_2$H$_4$OMe)$_2$] and the mixture stirred at 30° C. for 1 hour. the reaction mixture was extracted with dichloromethane and the solvent removed. The residue was extracted with ether-hexane and solvents removed. This residue was crystailised from 25 ml of hot ether by cooling to −20° C. giving 2.98 of red crystals. 2.41 g of the crude product was purified by chromatography on 60 cc of silica gel with 5% ethanol in ether. The first band was collected, reduced to dryness and crystallised from ether by cooling to −20° C. The yield of red crystals, Ru(S$_2$P{OC$_2$H$_4$OC$_2$H$_4$OMe}$_2$)$_3$, was 2.16 g, 56%. Analysis for C$_{30}$H$_{66}$O$_{18}$P$_3$RuS$_6$: Calc: C, 32.72; H, 6.04; S, 17.47. Found: C, 32.68; H, 6.08; S, 17.16.

In the in vitro tests, which were carried out in an atmosphere of argon, each compound (1×10$^4$ moles) was dissolved in double-distilled deionized and deoxygenated water. The resulting solution was placed in a three-necked pear-shaped flask and stirred by a magnetic stirrer at constant speed of 1000 rpm, at a constant temperature in the range 20° C.–24° C. A manometer was attached to the flask, and purified, dried nitric oxide gas (known volume in the range 3–5 cm$^3$) was introduced via a septum, using a gas syringe, at atmospheric pressure into the headspace above the reaction solution. The pressure within the flask was recorded periodically over a period of one hour.

A control experiment was carried out according to the above but without any complex present.

The recorded pressures in association with the results of the control experiment were analysed in order to determine the rate of NO uptake as a function of time for each compound tested.

On completion of each in vitro test, the reaction solution was freeze-dried. An infrared spectrum of the freeze-dried product provided information on metal-NO bond formation.

In the in vitro cell culture tests, murine (RAW264) macrophage cell lines, which can be induced to produce nitric oxide, were seeded, 10$^6$cells/well, onto 24 well culture plates of 2 ml volume per well, in Eagles modified minimal essential medium (MEM) plus 10% foetal bovine serum without phenol red.

The cells were activated to produce nitric oxide, with 10 μg/ml lipopolysaccharide and 100 units/ml interferon γ for 18 hours. Concurrently, test compounds made up in MEM were added at non-cytotoxic concentrations.

Control cells as above, which were activated to produce nitric oxide as above, but to which no test compound was added, were used as a measure of the amount of nitric oxide produced by the cells during the tests.

Background nitric oxide was assessed by measurement of nitrate and nitrite in cells which were not activated.

Cell viability was confirmed by Trypan blue dye exclusion at the end of the incubation period.

Nitric oxide was determined by measurement of nitrate and nitrite in the cell supernatant. These anions are the stable end-products of reactions of NO in solution. Such reactions may or may not be catalysed in biological systems. The sum of nitrite and nitrate concentrations gives the total NO production. Nitrite was determined using the Griess reaction in which nitrite reacts with 1% sulphanilamide in 5% H$_3$PO$_4$/0.1% naphthylethylenediamine dihydrochloride to form a chromophore absorbing at 540 nm. Nitrate was detemiined by reducing nitrate to nitrite with a bacterial nitrate reductase from *Pseudomonas oleovorans* and then measuring nitrite with the Griess reaction. In the absence of test compounds nitrite concentration plus nitrate concentration is equal to total nitric oxide production. The effect of test compounds on available nitric oxide (measured as nitrite+nitrate) was determined. The reduction in available nitric oxide compared with the control level may be taken as an indication of the degree of binding of NO by the test compounds.

In the ex vivo tests, segments of rat tail artery (0.8–1.5 cm) were dissected free from normotensive adult Wistar rats. The arteries were internally perfused with Krebs solution (mM: NaCl 118, KCl 4.7, NaHCO, 25, NaH$_2$PO$_4$ 1.15, CaCl$_2$ 2.5, MgCl$_2$ 1.1, glucose 5.6 and gassed with 95% O$_2$/5% CO$_2$ to maintain a pH of 7.4) in a constant flow perfusion apparatus. A differential pressure transducer located upstream of the vessel detected changes in back pressure. The rat tail artery preparation was pre-contracted with 6.5 μM phenylephrine to give a physiologically normal pressure of 100–120 mm Hg. The pre-contracted vessels were then perfused with the test compound. The arteries were perfused with Krebs solution between applications of test compound to wash out the test compound.

Pressure changes in the system served to indicate artery vasoconstriction. The vasoconstriction is a direct result of the removal of endogenous nitric oxide (edrf) from the endothelial cells of the rat tail artery.

RESULTS

The results of the in vitro, in vitro cell culture and ex-vivo tests were as follows:

IN VITRO TESTS

EXAMPLE 1

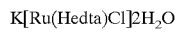

A pressure decrease indicated binding of NO to the metal compound. This is illustrated in FIG. 1.

The IR spectrum showed a peak at 1897 cm$^{-1}$, indicating the presence of a Ru—NO bond.

EXAMPLE 2

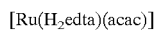

The IR spectrum showed a peak at 1896 cm$^{-1}$, indicating the presence of a Ru—NO bond.

EXAMPLE 3

K[Ru(hedtra)Cl]H$_2$O

A pressure decrease indicated binding of NO to the metal compound. This is illustrated in FIG. 1.

The IR spectrum showed a peak at 1889 cm$^{-1}$, indicating the presence of a Ru—NO bond.

EXAMPLE 4

K[Ru(dipic)$_2$]H$_2$O

A pressure decrease indicated binding of NO to the metal compound. This is illustrated in FIG. 1.

The IR spectrum showed a peak at 1915 cm$^{-1}$, indicating the presence of a Ru—NO bond.

EXAMPLE 5

(H$_2$pic)[RuCl$_2$(pic)$_2$](Hpic)H$_2$O

The IR spectrum showed a peak at 1888 cm$^{-1}$, indicating the presence of a Ru—NO bond.

EXAMPLE 6

K[Ru(H$_2$edta)Cl$_2$]H$_2$O

A pressure decrease indicated binding of NO to the metal compound. This is illustrated in FIG. 1.

The IR spectrum showed a peak at 1896 cm$^{-1}$, indicating the presence of a Ru—NO bond.

EXAMPLE 7

K[Ru(Hnta)$_2$]½H$_2$O

A pressure decrease indicated binding of NO to the metal compound. This is illustrated in FIG. 1.

The IR spectrum showed a peak at 1889 cm$^{-1}$, indicating the presence of a Ru—NO bond.

EXAMPLE 8

K[Ru(H$_2$dtpa)Cl]H$_2$O

A pressure decrease indicated binding of NO to the metal compound. This is illustrated in FIG. 1.

The IR spectrum showed a peak at 1905 cm$^{-1}$, indicating the presence of a Ru—NO bond.

EXAMPLE 9

[Ru$_3$O(lac)$_6$](lac)

The IR spectrum showed a peak at 1884 cm$^{-1}$, indicating the presence of a Ru—NO bond.

EXAMPLE 10

[Ru$_3$O(OAc)$_6$](OAc)

The IR spectrum showed a peak at 1877 cm$^{-1}$, indicating the presence of a Ru—NO bond.

EXAMPLE 11

[Ru$_2$(OAc)$_4$]NO$_3$

The IR spectrum showed a peak at 1891 cm$^{-1}$, indicating the presence of a Ru—NO bond.

EXAMPLE 12

[Ru(OCOEt)$_4$]NO$_3$

The IR spectrum showed a peak at 1891 cm$^{-1}$, indicating the presence of a Ru—NO bond.

EXAMPLE 13

K$_3$[Ru(ox)$_3$]

The IR spectrum showed a peak at 1889 cm$^{-1}$, indicating the presence of a Ru—NO bond.

EXAMPLE 14

[Ru$_2$(OAc)$_4$]Cl

The IR spectrum showed a peak at 1895 cm$^{-1}$, indicating the presence of a Ru—NO bond.

EXAMPLE 15

[Ru(NH$_3$)$_5$Cl]Cl$_2$

The IR spectrum showed two peaks at 1909 cm$^{-1}$ and 1928 cm$^{-1}$, indicating the presence of a Ru—NO bond.

EXAMPLE 16

[Ru(en)$_3$]I$_3$

The IR spectrum showed a peak at 1906 cm$^{-1}$, indicating the presence of a Ru—NO bond.

EXAMPLE 17

K[RuCl$_4$(phen)]H$_2$O

The IR spectrum showed a peak at 1904 cm$^{-1}$, indicating the presence of a Ru—NO bond.

EXAMPLE 18

[Ru(cyclam)Cl$_2$]Cl

The IR spectrum showed a peak at 1895 cm$^{-1}$, indicating the presence of a Ru—NO bond.

EXAMPLE 19

K[RuCl$_4$(bipy)]

The IR spectrum showed a peak at 1885 cm$^{-1}$, indicating the presence of a Ru—NO bond.

EXAMPLE 20

[RuCl$_3$(dmso)$_2$(NH$_3$)]

The IR spectrum showed a peak at 1889 cm$^{-1}$, indicating the presence of a Ru—NO bond.

EXAMPLE 21

[Ru(NH$_3$)$_6$]Cl$_3$

The IR spectrum showed a peak at 1910 cm$^{-1}$, indicating the presence of a Ru—NO bond.

EXAMPLE 22

cis-[RuCl$_2$(dmso)$_4$]

The IR spectrum showed a peak at 188 cm$^{-1}$, indicating the presence of a Ru—NO bond.

EXAMPLE 23

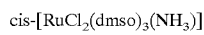
cis-[RuCl$_2$(dmso)$_3$(NH$_3$)]

The IR spectrum showed a peak at 1893 cm$^{-1}$, indicating the presence of a Ru—NO bond.

EXAMPLE 24

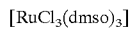
[RuCl$_3$(dmso)$_3$]

The IR spectrum showed a peak at 1880 cm$^{-1}$, indicating the presence of a Ru—NO bond.

EXAMPLE 25

[Ru(mtc)$_3$]

The IR spectrum showed a peak at 1862 cm$^{-1}$, indicating the presence of a Ru—NO bond.

EXAMPLE 26

[Ru(maltol)$_3$]

The IR spectrum showed a peak at 1866 cm$^{-1}$, indicating the presence of a Ru—NO bond.

EXAMPLE 27

[Ru(acac)$_2$(MeCN)$_2$]CF$_3$SO$_3$

The IR spectrum showed a peak at 1899 cm$^{-1}$, indicating the presence of a Ru—NO bond.

EXAMPLE 28

K$_2$[RuCl$_5$(H$_2$O)]

The IR spectrum showed a peak at 1903 cm$^{-1}$, indicating the presence of a Ru—NO bond.

EXAMPLE 29

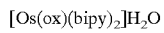
[Os(ox)(bipy)$_2$]H$_2$O

The IR spectrum showed a peak at 1894 cm$^{-1}$, indicating the presence of a Os—NO bond.

IN VITRO CELL CULTURE TESTS

Results are shown in Table 1 and FIG. 2.

EXAMPLE 1

K[Ru(Hedta)Cl]2H$_2$O

Available nitric oxide was reduced in a dose-dependent fashion with a maximum reduction of 75% at a concentration of 100 μM.

EXAMPLE 2

[Ru(H$_2$edta)(acac)]

Available nitric oxide was reduced by 82% at 100 μM test compound.

EXAMPLE 3

K[Ru(Hedtra)Cl]H$_2$O

Available nitric oxide was reduced by 42% at 100 μM.

EXAMPLE 6

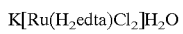
K[Ru(H$_2$edta)Cl$_2$]H$_2$O

Available nitric oxide was reduced by 77% at 100 μM test compound.

Example 14

[Ru$_2$(OAc)$_4$]Cl

Available nitric oxide was reduced by 47% at 10 μM.

EXAMPLE 15

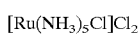
[Ru(NH$_3$)$_5$Cl]Cl$_2$

Available nitric oxide was reduced by 86% at 100 μM test compound.

EXAMPLE 26

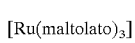
[Ru(maltolato)$_3$]

Available nitric oxide was reduced by 71% at 100 μM.

TABLE 1

| | | % Decrease of Available Nitric Oxide |
|---|---|---|
| Example 1 | 25 μM | 12 |
| | 50 μM | 23 |
| | 100 μM | 75 |
| Example 2 | 100 μM | 82 |
| Example 3 | 100 μM | 42 |
| Example 6 | 100 μM | 77 |
| Example 14 | 100 μM | 47 |

TABLE 1-continued

| | | % Decrease of Available Nitric Oxide |
|---|---|---|
| Example 15 | 100 μM | 86 |
| Example 26 | 100 μM | 71 |

EX-VIVO TESTS

EXAMPLE 2

Application of test compound resulted in a dose-dependent vasoconstriction at 10 μM and 100 μM. This effect was reversible by washout with Krebs solution.

EXAMPLE 3

Application of test compound resulted in a dose-dependent vasoconstriction at 10 μM and 100 μM. This effect was reversible by washout with Krebs solution.

EXAMPLE 14

Application of test compound resulted in a dose-dependent vasoconstriction at 10 μM and 100 μM. This effect was reversible by washout with Krebs solution.

EXAMPLE 15

Application of test compound resulted in a dose-dependent vasoconstriction at 10 μM and 100 μM. This effect was reversible by washout with Krebs solution.

EXAMPLE 26

Application of test compound resulted in a dose-dependent vasoconstriction at 10 μM and 100 μM and 1000 μM. This effect was reversible by washout with Krebs solution.

TABLE 2

| | | % Vasoconstriction |
|---|---|---|
| Example 2 | 10 μM | 20 |
| | 100 μM | 69 |
| Example 3 | 10 μM | 17 |
| | 100 μM | 59 |
| Example 14 | 10 μM | 11 |
| | 100 μM | 40 |
| Example 15 | 10 μM | 16 |
| | 100 μM | 86 |
| Example 26 | 10 μM | 10 |
| | 100 μM | 18 |
| | 1000 μM | 25 |

What is claimed is:

1. A method for preparing a pharmaceutical composition comprising formulating a neutral, anionic or cationic metal complex having at least one site for coordination with NO, of formula:

$$[M_a(X_bL)_cY_dZ_e]^{n\pm}$$ (formula I), with a pharmaceutically acceptable carrier, wherein the complex is present in an amount sufficient for attenuation of NO levels where NO is implicated in disease, and wherein:

M is a metal ion or a mixture of metal ions;

X is a cation or a mixture of cations;

L is a ligand, or mixture of ligands each containing at least two different donor atoms selected from the elements of Group IV, Group V or Group VI of the Periodic Table;

Y is a ligand, or a mixture of the same or different ligands each containing at least one donor atom or more than one donor atom, which donor atom is selected from the elements of Group IV, Group V or Group VI of the Periodic Table;

and

Z is a halide or pseudohalide ion or a mixture of halide ions and pseudohalide ions;

$a=1-3$; $b=0-12$; $c=0-18$; $d=0-18$; $e=0-18$; and $n=0-10$;

provided that at least one of c, d and e is 1 or more;

and where c is 0; b is also 0;

and where a is 1; c, d and e are not greater than 9;

and where a is 2; c, d and e are not greater than 12.

2. A pharmaceutical composition containing an optionally hydrated ruthenium complex as described in claim 1, wherein the complex is present in an amount sufficient for attenuation of NO levels where NO is implicated in disease and wherein:

M is Ruthenium;

X is hydrogen;

L is an amide or ester or derivative thereof, or a polydentate aminocarboxylate ligand, for example edda, tropolone edta, nta, dipic, pic, dtpa, hedtra, tedta or dtedta or a mixture of any of these;

Y is as defined above and may for example be selected from acetylacetone (acac), a β-diketonate, water, dimethylsulphoxide (dmso), carboxylate, bidentate carboxylate, catechol, kojic acid, maltol, hydroxide, tropolone, malonic acid, oxalic acid, 2,3-dihydroxynaphthalene, squaric acid, acetate, a sulphate and a glycolate;

Z is Chloride;

$a=1$; $b=0-6$; $c=1-3$; $d=0-2$; $e=0-4$; and $n=0-4$, provided that at least one of c, d and e is 1 or more;

where c is 0; b is also 0; and where a is 1; c, d and e are not greater than 9.

3. A pharmaceutical composition containing an optionally hydrated complex of ruthenium as described in claim 1, wherein M is ruthenium and Y is an oxygen donor ligand selected from the group consisting of: acetate, lactate, oxide, propionate and maltolate and wherein $a=1-3$; $b=0$; $c=0$; $d=1-18$; $e=0-8$ and $n=0-6$ and the complex is present in an amount sufficient for attenuation of NO levels where NO is implicated in disease.

4. A pharmaceutical composition containing an optionally hydrated complex of ruthenium as described in claim 1, wherein M is ruthenium and Y is a nitrogen donor ligand selected from the group consisting of: en, py, phen, bipy, cyclam or oep and wherein $a=1$; $b=0$; $c=0$; $d=1-9$; $e=1-9$ and $n=0-4$ and the complex is present in an amount sufficient for attenuation of NO levels where NO is implicated in disease.

* * * * *